United States Patent [19]
Briggs

[11] Patent Number: 4,676,640
[45] Date of Patent: Jun. 30, 1987

[54] FLUCTUATION ANALYSIS FOR ENHANCED PARTICLE DETECTION

[75] Inventor: Jonathan Briggs, Palo Alto, Calif.

[73] Assignee: Syntex (U.S.A.) Inc., Palo Alto, Calif.

[21] Appl. No.: 650,320

[22] Filed: Sep. 12, 1984

[51] Int. Cl.$^4$ ............................................. G01N 21/64
[52] U.S. Cl. ................................. 356/317; 250/458.1; 250/459.1; 250/461.2; 356/318; 356/417; 364/554; 364/819
[58] Field of Search ............... 250/461.2, 458.1, 459.1; 356/317, 318, 417; 436/172; 364/554, 555, 604, 819, 824

[56] References Cited

U.S. PATENT DOCUMENTS

| 3,941,479 | 3/1976 | Whitehead | 356/335 |
| 4,178,917 | 12/1979 | Shapiro | 356/317 |
| 4,407,964 | 10/1983 | Elings et al. | 356/318 |
| 4,421,860 | 12/1983 | Elings et al. | 356/318 |
| 4,537,861 | 8/1985 | Elings et al. | 356/317 |
| 4,560,881 | 12/1985 | Briggs | 250/458.1 |
| 4,564,598 | 1/1986 | Briggs | 436/172 |

OTHER PUBLICATIONS

Fannin, *Electronic Circuits and Systems*, V. 3, N. 1, Jan. 1979, pp. 15-20.
Betty et al., *Anal. Chem.*, V. 48, N. 13, Nov. 1976, p. 1899.
Kam et al., *Rev. Sci. Instrum.*, vol. 46, No. 3, Mar. 1975, p. 269.

Primary Examiner—F. L. Evans
Attorney, Agent, or Firm—Theodore J. Leitereg

[57] ABSTRACT

An improvement is disclosed in a method for measuring intensity fluctuations of an electromagnetic signal of wavelength between about 350 nm to 1200 nm from a liquid medium. The improvement comprises autocorrelating the intensity of the signal over a non-zero interval the duration of which is short compared to the mean duration of the fluctuations. The method has particular applciations in the diagnostic area, particularly where such fluctuations are a result of the presence of fluroscent particles in a liquid medium. Methods are also disclosed for determining an analyte in a sample suspected of containing such analyte.

25 Claims, 1 Drawing Figure

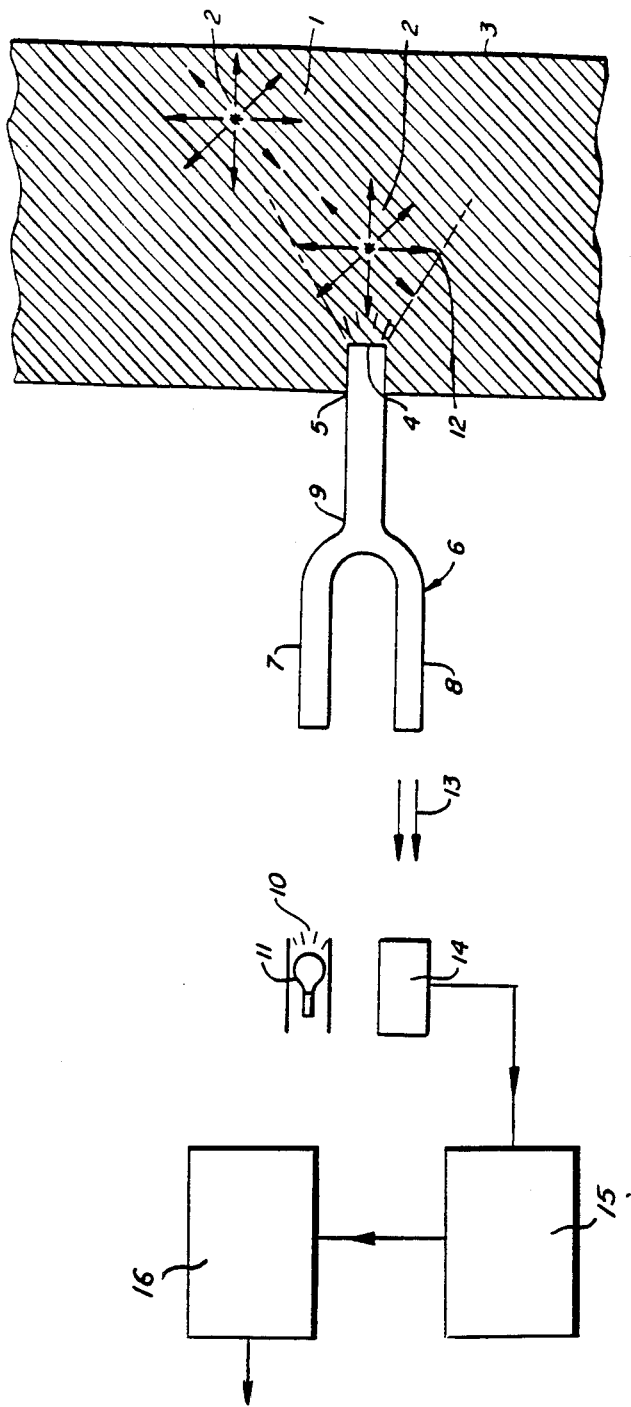
FIGURE

FLUCTUATION ANALYSIS FOR ENHANCED PARTICLE DETECTION

BACKGROUND OF THE INVENTION

1. Field of the Invention

The counting of particles in fluid suspensions by fluorescent emission has a wide range of applicability in immunoassay techniques and in the characterization of biological materials in general. Known methods, however, require specially designed orifices, flow conduits, or sensing zones, or complex computational techniques to differentiate the particles of interest from extraneous or undesired components in the sample.

There is thus a need for an inexpensive yet accurate technique which provides a direct indication of particle presence, concentration and/or size, particularly where particles are being detected with low signal to noise ratio.

2. Description of the Prior Art

The use of flow cytometers involving the carefully controlled flow of a cell suspension through a narrow flow channel is described in Miller, et al., "Usage of the Flow Cytometer-Cell Sorter," *Journal of Immunological Methods*, 47, 13-24 (1981); Hoffman, et al., "Immunofluorescent Analysis of Blood Cells by Flow Cytometry," *Int. J. Immunopharmac.*, 3(3), 249-254 (1981); a general review of flow cytometry is found in *Flow Cytometry and Sorting*, M. R. Melamed, P. E. Mullaney and M. L. Mendelsohn, Eds., J. Wiley & Sons, N.Y., N.Y. 1979; Hansen, et al., U.S. Pat. No. 4,284,355, issued Aug. 18, 1981; Hansen, et al., U.S. Pat. No. 4,284,412, issued Aug. 18, 1981; Auer, et al., U.S. Pat. No. 4,284,924, issued Aug. 4, 1981; and Stevens, U.S. Pat. No. 3,275,834, issued Sept. 27, 1966.

The use of laser beams and slits to differentiate particles based on their relative size by the correlation of fluorescence fluctuations in a relatively large sample volume is described in: Briggs, et al., "Homogeneous Fluorescent Immunoassay," *Science*, 212, 1266-1267 (1981) and Nicoli, et al., "Fluorescence Immunoassay Based on Long Time Correlations of Number Fluctuations," *Proc. Natl. Acad. Sci. U.S.A.*, 77(8), 4904-4908 (1980).

U.S. Pat. No. 4,421,860 (Elings, et al.) describes a homogeneous fluoroimmunoassay involving autocorrelation processing of optically sensed signals. U.S. Pat. No. 4,407,964 (Elings, et al.) discloses a homogeneous fluoroimmunoassay involving sensing radiation for forward and back directions.

An immunological reagent and radioimmunoassay are disclosed by Dreyer in U.S. Pat. No. 3,853,987.

SUMMARY OF THE INVENTION

In its broadest aspect, the method of the present invention is useful for measuring intensity fluctuations of an electromagnetic signal of wavelength between about 350 nm to 1,200 nm from a liquid medium. In the present method, the intensity of such signals is autocorrelated over a non-zero interval the duration of which is short compared to the mean duration of the fluctuations.

In a particular application of the method of the present invention, fluctuations of fluorescence intensity values in a liquid medium are measured, where such fluctuations are a result of the presence in the liquid medium of fluorescent particles. The fluorescence intensity values obtained at a plurality of collection intervals are autocorrelated. Temporally adjacent intervals provide values for the fluorescence intensity of partially overlapping volumes of the liquid medium wherein the volumes contain relatively few fluorescent particles. The improvement of the present invention results from using a collection interval the duration of which is less than the mean residence time of a fluorescent particle in such volume and the autocorrelation interval is equal to or a small multiple or a fraction of the collection interval.

The improved method of the present invention has specific application to the determination of an analyte in a sample suspected of containing such analyte. The sample is combined with an assay reagent to provide an assay mixture containing fluorescent particles where the fluorescent intensities of the particles are related to the presence of the analyte. A plurality of partially overlapping volumes of the sample are irradiated with a light of wavelength between about 250 nm and 1200 nm. The irradiated sample volume has relatively few fluorescent particles. The fluorescence intensity values at a plurality of equal fluorescence collection intervals is determined, the duration of such fluorescence collection intervals being less than the mean residence time of a fluorescent particle within the irradiated sample volume. The fluorescence intensity values at the collection intervals are autocorrelated over an autocorrelation time interval that is equal to or a small multiple or a fraction of the collection interval. The autocorrelated fluorescence intensity values are then related to similarly autocorrelated fluorescence intensity values from an assay medium having a known amount of analyte.

BRIEF DESCRIPTION OF THE DRAWING

The attached drawing is a simplified schematic view of one embodiment of the apparatus of the present invention for use in detecting the presence of fluorescing particles.

DESCRIPTION OF THE SPECIFIC EMBODIMENTS

The present method provides an improvement in methods for measuring intensity fluctuations of an electromagnetic signal of wavelength between about 350 nm to 1200 nm from a liquid medium. The improvement comprises autocorrelating the intensity of the signal over a non-zero interval the duration of which is short compared to the mean duration of the fluctuations.

The present invention has application in the detection of intensity fluctuations resulting, e.g., from fluorescence particles, where there is low signal to noise ratio. Signal magnitudes are often registered in terms of the number of counts in a fixed time interval; for example, number of photo-counts per time interval as a measure of light intensity (as in photon counting). Even when analog detection is used, the signal is generally proportional to n where n equals the number of counts per fixed time interval. By continuously monitoring n, excessive fluctuations can be observed as an indication of the presence in the sample of particles giving off large signals. This is useful in techniques where a small sampling volume is used to detect the fluorescence from one or a few particles (or cells), such as in, for example, flow cytometry or fiber optic probe cytometer. A standard measure for the size of fluctuations is obtained by calculating the mean-square of the measured signal, $<n_i^2>$, where the subscript i denotes that an ensemble of counts is used, each one being squared before the average is calculated (denoted by the pointed brackets). If a typical value of n is given by $n_i = \bar{n} + \delta n_i$, where $\bar{n}$ is the mean and $\delta n_i$ is the fluctuation, then $$\begin{aligned}<n_i^2> &= <(\bar{n}+\delta n_i)^2> \\ &= <\bar{n}^2 + 2\bar{n}\delta n_i + \delta n_i^2> \\ &= <\bar{n}^2> + <\delta n_i^2< \\ &= \bar{n}^2 + <\delta n_i^2>,\end{aligned}$$

where $<\bar{n}> = \bar{n}$ and $<n\delta \bar{n}_i> = \bar{n}<\delta n_i> = 0$. Then, the absolute size of the fluctuations is characterized by the standard deviation $$\sigma = [<n_i^2> - \bar{n}^2]^{\frac{1}{2}} = [<\delta n_i^2>]^{\frac{1}{2}}$$

and the relative size is given by the coefficient of variation (C.V.) which equals $\sigma/\bar{n}$. The C.V. of an ensemble of readings from a small sample volume, as particles pass through, would be an indication of whether or not the individual particles give off a signal. The sensitivity of this procedure will depend upon the size of the C.V. with a sample when the particles produce little or no signal.

The primary background contribution to the C.V. is Poisson number fluctuations. Even if the true signal is unvarying, successive readings of that signal by counting events will fluctuate with $$\sigma_{Poisson} = [\bar{n}]^{\frac{1}{2}}$$

This means that the relative size of the background fluctuations is $$(C.V.)_{Poisson} = \bar{n}^{-\frac{1}{2}}$$

In low signal (small n) situations, the C.V. will be inherently large and therefore not a sensitive indicator for the presence of weakly labeled particles (particles that give a weak signal).

The subject of this invention is an improvement in the method of calculating the relative size of the fluctuations of the signal, such that the Poisson fluctuations do not contribute. A collection interval is selected for counting the discrete events (e.g., photo-counts) such that between two adjacent collection intervals the particle distribution in a small sampling volume is relatively constant. That is, a collection interval is selected which is short compared to the particle duration time in the sampling volume. Then, instead of using the square of an individual reading to calculate the C.V., the product of readings from adjacent collection intervals is used.

In the present method the calculation of the relative size of fluctuations uses the autocorrelation function of readings separated by a time interval short compared to the particle duration time. In this way, only fluctuations which are correlated over this finite interval will contribute. Since Poisson fluctuations are totally uncorrelated between independent collection intervals, the Poisson background fluctuations will not contribute. However, since the particle configuration in the sample interval will be relatively unchanged over two adjacent collection intervals, signal from particles will contribute.

The fluctuations are evaluated in accordance with the present invention using the formula- $$(C.V.)_p = \frac{[C(t) - <n>^2]^{\frac{1}{2}}}{<n>}$$

where $(C.V.)_p$ is the coefficient of variation for a particle, n is the photo count (proportional to the fluorescence intensity), $< >$ denotes taking an average over an ensemble of consecutive collection intervals, and $C(t)$ is the autocorrelation of photo counts over collection intervals separated by the autocorrelation interval t.

In the prior art methods where autocorrelation functions have been used to analyze signal fluctuations in order to detect the presence of relatively large particles, the exact same sampling volume was sensed periodically. The autocorrelation function of the signal was calculated where the correlation time equaled the period of repetitive samples (1 to 10 sec.). Relatively large particles diffuse slowly enough so that their configuration will be unchanged over the long correlation time. Their signal will contribute to the autocorrelation function. However, small particles (e.g., free molecules) will randomize during this period and thus not contribute. These studies used a long correlation interval to distinguish between free and bound signal. In order to obtain a statiscally significant correlation function, the total measurement time had to be long compared to the correlation time (typically 1000 periods or $10^3$ to $10^4$ sec.).

In the prior art one of the traditional measures of the relative size of the fluctuations uses the autocorrelation function of readings with zero time difference. In that approach, all types of fluctuations will contribute.

Before proceeding further with a description of the present invention, a number of terms will be defined.

"Fluctuations of an electromagnetic signal"—the shifting back and forth of an electromagnetic signal. The electromagnetic signal may be as a result of fluorescence, scattered light, transmitted light, or the like. Fluctuations in fluorescence occur normally in continuous media and may be increased by various combinations of particles and continuous media. For example, in liquids the combinations can include fluorescent particles in a relatively less fluorescent liquid, non-homogeneously fluorescent particles in a fluorescent or non fluorescent liquid or particles in a fluorescent liquid which particles are relatively less fluorescent than the liquid. Furthermore, the fluorescent fluctuation in liquids may be as a result of aggregation of particles, non-fluorescent particles becoming fluorescent, fluorescent particles becoming non-fluorescent or changes in the fluorescence of the liquid. The particles may be comprised of polymers, both naturally occuring or synthetic, natural particles, such as virions and cells, for example, blood cells and bacteria, latex particles, or the like. Particle sizes may vary from 0.05 to 100 microns, where synthetic particles will generally be from about 0.1 microns to 10 microns in diameter. The term "fluctuations of electromagnetic signal" includes fluctuations of fluorescence intensity values in a liquid medium. Other fluctuations of an electromagnetic signal may be the result of variations in the elastically scattered light from particles, cells, etc., in a liquid medium or variations in the transmitted light between a source and a detector due to the passage of particles.

A fluorescent signal may be obtained by the use of any conventional fluorescing compound. Particles emitting fluorescence can be obtained by binding a fluorescing compound to the particle surface or by using particles which exist in their natural state with fluorescent components on the surface. Typical fluorescers include xanthene dyes, such as fluoresceins, rosamines, and rhodamines, naphthylamines, coumarin derivatives, such as 3-phenyl-7-hydroxycoumarin, 4-methyl-7-dimethylaminocoumarin and 4-methyl-7-methoxy coumarin, stilbene derivatives such as 4-dimethylamino-4'-cyano stilbene and pyrenes. Descriptions of fluorescers can be found in Brand, et al., *Ann. Rev. Bio. Chem.*, 41:843-868 (1972) and Stryer, *Science,* 162:526 (1968).

"Autocorrelation" of the intensity fluctuations of an electromagnetic signal—A convenient way to monitor fluctuations of a signal is to evaluate the familiar intensity autocorrelation function, $$C(t) = <n(t')n(t'-t)>_{t'}$$

in which n(t') is the number of photo-counts per collection interval at time t' and n is proportional to the intensity and the symbol $<\ldots>_{t'}$ indicates an average of the intensity product over a large number of sampling times t'.

The autocorrelation is determined by obtaining an electronic signal proportional to the number of photopulses occuring during a given collection interval and averaging a large number of products of two said signals, obtained in two different collection intervals, said collection intervals temporally separated by the correlation interval, t.

"Collection interval"—The period of time during which photo-pulses are counted, also referred to as "gate time". The duration of the collection interval will be less than the mean duration of the intensity fluctuation of the electromagnetic signal, for example, less than the means residence time of a fluorescent particle within a specified volume. The collection interval will generally lie within the range of about 0.01 to 100 milliseconds, more usually from about 1 to 10 milliseconds.

"Effective volume"—a volume in the liquid medium in which the electromagnetic signal is sensed. Generally, the effective volume contains relatively few particles of interest. In its simplest form, there is a low probability of finding more than one particle of interest in the effective sample volume.

"Analyte"—the compound, particle, or composition to be measured, which may be a cell, organelle, microrganism, and may contain or be a member of a specific binding pair (sbp) and may be a ligand, which is mono- or polyvalent, that is, having one or a plurality of determinant sites, an antigen, a single compound or plurality of compounds which share at least one common determinant site; or a receptor.

"Sbp member"—A member of a specific binding pair, consisting of two different molecules, where one of the molecules has an area on the surface or in a cavity which specifically binds to a particular spatial and polar organization of the other molecule. The sbp members are referred to as ligand and receptor (anti-ligand) and members of a specific binding pair are referred to as homologous.

"Ligand"—Any organic compound for which a receptor naturally exists or can be prepared.

"Receptor (anti-ligand)"—Any macromolecular compound or composition capable of recognizing (having an enhanced binding affinity to) a particular spatial and polar organization of a molecule, i.e., epitopic or determinant site. Illustrative receptors include naturally occurring receptors, e.g., thyroxine-binding globulin, antibodies, enzymes, Fab fragments, lectins, and the like. The term "antibody" is employed in this case as illustrative of, and to more generally denote, receptor.

"Cell"—Any one of the minute protoplasmic masses which make up organized tissue, comprising a mass of protoplasm surrounded by a membrane including nucleated and unnucleated cells, organelles, spores, and ovocytes.

The present invention has particular application for determining an analyte in a sample suspected of containing the analyte. The sample is combined with an assay reagent to provide an assay mixture containing particles where the fluorescent intensities of the particles or solution are related to the presence of the analyte. The particles may be directly added to the sample as part of the assay reagent or the particles may be part of the sample such as, e.g., where the sample contains cells. On the other hand, the particles may be formed as a result of the mixing of the assay reagent with the sample by, for example, agglutination or the like. Broadly defined, the assay reagent contains those agents, which upon combination with the sample, provide an assay mixture containing particles where the fluorescent intensities of the particles or solution are related to the presence of the analyte in the sample.

A plurality of partially overlapping effective volumes of said sample is sequentially irradiated with a wavelength of light between about 250 nm and 1200 nm, preferably about 325 nm to 700 nm. The term "partially overlapping" means that some of the liquid medium will be common to consecutively sampled effective volumes. That is to say, partially overlapping effective volumes means that a given particle will contribute to the recorded signal of more than one consecutive collection intervals.

One means for irradiating the overlapping effective volumes is to employ a method and apparatus described in U.S. patent application Ser. No. 397,285, filed July 12, 1982, now U.S. Pat. No. 4,564,598 the disclosure of which is incorporated herein in its entirety by reference thereto. Basically, the effective volume is irradiated employing an optical fiber where the effective volume is determined by the construction of the optical fiber. The shape of the volume will normally be conical. The optical fibers are typically constructed of a core region and one cladding region, whose thickness (diameter) and relative refractive indices determine both the half angle of the cone and the cone's smallest diameter at the tip of the fiber. The effective axial length is determined by the intensity of the excitation beam and the rate of drop in intensity of the excitation light with increasing axial distance from the fiber tip. The rate depends upon the half angle of the cone, with larger half angles causing greater rates of intensity drop and, hence, shorter effective cone lengths. Also affecting the intensity drop will be light scattering and absorption properties of the medium.

The various parameters affecting the observed signal will be chosen to insure that a reasonable threshold value is available for an effective sample volume, which will allow for discrimination against background signals.

The different effective volumes may be as a result of an extended period of time which allows for diffusion of particles in and out of the sample volume or having a plurality of optical fibers, each one receiving signals from different effective volumes. Alternatively, a dynamic system may be used where the sample flows by one or more optical fibers or one or more optical fibers move through the sample.

The excitation light may be provided by irradiating the entire sample or a major portion of the sample with excitation light. Alternatively, and preferably, the excitation light may be provided by the optical fiber so that the sample volume will be proportional to the volume irradiated.

A particularly useful optical fiber device is the commercially available device known as a coupler or multiplexer, consisting of three optical fibers joined to form a bifurcated conduit with three terminal ports, conveniently referred to as an input port into which excitation light is fed, a probe port which is submerged in the sample and a detector port. In a form convenient for use in the present invention, the fibers are joined in such a manner that substantially all light entering the input port is transmitted to the probe port. Light entering the probe port, as from the fluorescent emission, may be split at the conduit juncture so that a portion will travel to the input port and a second portion to the detector port. Alternatively, a dichroic mirror can be utilized at the juncture directing substantially all of the fluorescent light to the detector port. Such devices are available from commercial suppliers, for example, Kaptron, Inc., Palo Alto, Calif.

In the next step in a particular embodiment of the present invention, the fluorescence intensity values at a plurality of equal fluorescence collection intervals is determined. The duration of the fluorescence collection intervals generally is less than the residence time of the fluorescence particle in the irradiated sample volume. Preferably, the fluorescence intensity values are determined using the optical fiber described above.

In the next step in the present method, the fluorescence intensity values at the collection intervals mentioned above are autocorrelated over a correlation time interval which is equal to or a small, preferably integral, multiple or a fraction of the collection interval, preferably, from about 1 to 10 times, more preferably, from about 1 to 3 times, the collection interval. Generally, the correlation interval is equal to or greater than the duration of one collection interval and less than the residence time of a fluorescent particle within the irradiated sample volume. The correlation interval is usually one-third to one one-hundredth, preferably one-third to one-tenth, the residence time of the fluorescent particle within the irradiated sample volume.

Next, the correlated fluorescence intensity values can be related to similarly correlated fluorescence intensity values from an assay medium having a known amount of analyte. The autocorrelation function and the relation of the results from the known and unknown samples can be carried out with the use of a computer which will contain the appropriate program for carrying out the autocorrelation functions. Thus, the computer will then automatically calculate the concentration of analyte in the sample based on the above determination.

By employing the above-described method in a fluorescence assay, a large number of protocols and reagents may be employed. One group of protocols will involve measuring fluorescent particles. This group can be divided into assays in which (1) the analyte is comprised of fluorescent particles that have unique absorption and/or emission relative to any other fluorescent particles in the medium and can therefore be detected directly by their fluorescence fluctuations; (2) either analyte or a complementary sbp member of the analyte is attached to fluorescent particles where the sbp member on the particle and a complementary sbp member bind to cause aggregation of the particles and produce a corresponding change in the fluctuations; (3) either the analyte or a complementary sbp member of the analyte is attached to nonfluorescent particles when an sbp member complementary to the sbp member on the particles is either fluorescent or is made fluorescent by specific binding or reaction of a fluorescent reagent as, for example, a third fluorescer-labeled sbp member; (4) either the analyte or an sbp member of the analyte is attached to non-fluorescent particles where an sbp member complementary to the sbp member on the particles causes agglutination of the particles and a change in fluorescence fluctuation is brought about by the resulting particulate aggregates displacing an equal volume of a solution containing a dissolved fluorescent dye.

The above techniques are only illustrative of a few of the many types of assays available for determining analytes. These assays may be found in a number of articles and patents, a few of the patents being illustrated by U.S. Pat. Nos. 3,826,613; 3,853,987; 3,925,541; 4,061,466; 5,062,935; 4,141,965; 4,164,558; 4,256,834; 4,275,149; and 4,318,707. The description of the various methods is incorporated herein by reference, these descriptions not intended to be exhaustive, but rather illustrative of the variety of methods to which the subject invention may be applied.

The invention further includes an apparatus for determining an analyte in a sample suspected of containing said analyte, where said analyte is a member of specific binding pair ("sbp member") consisting of ligand and its homologous receptor. The appatatus comprises (a) a means for irradiating sequentially a plurality of partially overlapping volumes of said sample with a wavelength of light between about 250 nm and 1200 nm by means of an optical fiber, said samples having been combined with an assay reagent to provide an assay mixture containing fluorescent particles which result from the binding between sbp members in proportion to the amount of analyte in said medium; (b) means for determining the fluorescence intensity values at a plurality of equal fluorescence collection intervals, the duration of said fluorescence collection intervals being less than the mean time of a fluorescent particle within an irradiated sample volume; (c) means for continuously autocorrelating the fluorescence intensity values at said collection intervals which means may be software or dedicated hardware; and (d) means for relating the autocorrelated fluorescence intensity values to similarly autocorrelated fluorescence intensity values from an assay medium containing a known amount of analyte.

A further understanding of the apparatus may be achieved by reference to the attached drawing, which illustrates an embodiment of the invention as it could be used in an assay. A liquid sample 1 containing the particles 2 in suspension is contained in a sample receiving means 3. The sample receiving means may be any vessel capable of holding the sample and receiving the tip 4 of an optical fiber 5 below the liquid surface. Vessels of small size, such as microtiter wells, are useful here.

The juncture 9 directs substantially all of the light from input fiber 7 to probe fiber 5 from which the light enters the liquid sample 1 through probe tip 4 to irradiate an effective sample volume 12. Only a portion of the fluorescent light from the signal particle shown inside the effective sample volume 12 is emitted in an appropriate direction to re-enter the probe fiber tip. This portion is then transmitted back through the probe fiber 5 to the coupler juncture 9, where it is either split equally or at some fixed ratio between input fiber 7 and detector fiber 8, such that a signal 13 is provided at the exit of the detector fiber 8 of sufficient intensity to be read by a detector 14 and distinguished from background noise. The detector is any device capable of receiving photons and converting them to a form which permits differentiation between signals of different intensities. A photomultiplier is a typical example.

The signal exiting detector 14 is transmitted to means 15 for continuously autocorrelating the fluorescent intensity values at the collection intervals, which means may be software or dedicated hardware. The data from means 15 is transmitted to means 16 for relating the autocorrelated fluorescence intensity values to similarly autocorrelated fluorescence intensity values from an assay medium containing a known amount of analyte. The values are read from means 16.

EXAMPLES

The invention is further demonstrated by the following illustrative example which is provided by way of illustration and not limitation.

EXAMPLE

A homogeneous fluorescence assay was performed for the A group antigen of human red blood cells (RBCs). In the assay, 50 μl of whole blood was incubated for 10 minutes with 50 μl of fluorescent labeled (fluorescein isothiocyanate-FITC) anti-A antibody (monoclonal IgM, Chembiomed, Edmonton, Alberta). The sample was then diluted with 7.5 ml of buffer (0.1M sodium bicarbonate, 20 mM EDTA, 0.17 bovine serum albumin (BSA), pH 8.5) and read with the fiber optic probe cytometer.

The probe fiber of a "Y"-shaped fiber optics multiplexer obtained from Kaptron, Inc., Palo Alto, Calif., was submerged in the suspension. The fiber had a diameter of 50 microns and produced an excitation cone with a half angle of 12° and an effective sampling volume of $1 \times 10^{-7}$ ml. Excitation light from a He-Cd laser was fed into one of the two branch fibers and was transferred to the probe fiber by the multiplexer. A cone of excitation light emanated from the probe which was mechanically scanned through the sample. The portion of the fluorescence emitted from the sample volume which re-entered the submerged fiber probe was transferred to the second branch fiber by the multiplexer, which was coupled to a high gain photomultipler after filtering, which filtering attenuates light at the excitation wavelengths in favor of light at the fluorescent emission wavelengths.

The fiber probe was moved through the cell suspension at about 1 cm/sec; this means that a given cell was under the fiber tip, in the sampling volume, for about 5 ms. Fluorescence from the fiber probe was recorded every 1 ms (the collection interval), in terms of the number of photo-counts per ms (n). For this assay, the mean of that number was typically 45. In 1000 consecutive readings, the fluctuations relative to the mean value of the readings were analyzed by two methods. For a given assay, the degree of fluctuations for 10 separate blocks of 1000 readings were averaged to give the final result.

Before describing the two methods of analysis for the fluctuations, the relationship between the fluorescence fluctuations and whether the sample is positive or negative should be understood. If the blood was group A (positive sample), then the fluorescence will partition from being free in solution to being bound to RBCs, via the antibody-cell surface antigen reaction. The fluorescent cells passing in front of the fiber probe will generate a fluctuating signal. However, if the blood was group B or O (negative samples), then the fluorescence would remain free in solution and the fiber probe would sense a more uniform signal. So in this assay, a large amount of fluorescence fluctuations corresponds to a positive sample.

The fluctuations were evaluated using a known method. The coefficient of variation (C.V.) of the photocounts per collection interval (1 ms) was evaluated using the formula—

$$(C.V.) = \frac{[<n_i^2> - <n>^2]^{\frac{1}{2}}}{<n_i>} = \frac{\sigma}{n}$$

where $n_i$ is the photo-count (proportional to the fluorescent intensity) during the $i^{th}$ collection interval and $< >$ denote taking the average over an ensemble of consecutive collection intervals. The subscript T refers to the fact that this approach is a total C.V.; that is, all types of fluctuations will contribute. The total C.V. can be rewritten in terms of the correlation function, relating photo-counts taken at different times, $$(C.V.)_T = \frac{[C(0) - <n>^2]^{\frac{1}{2}}}{<n>}$$

$$C(t) = <n(t')n(t' - t)>_{t'}$$

Note that the total C.V. involves the correlation function at zero time difference, t=0.

The fluctuations were evaluated in accordance with the present invention using the formula—

$$(C.V.)_p = \frac{[C(\Delta t) - <n>^2]^{\frac{1}{2}}}{<n>}$$

where (C.V.)p is the coefficient of variation for a particle, n is the photo count (proportional to the fluorescence intensity), $< >$ denotes taking an average over an ensemble of consecutive collection intervals, and C(t) is the autocorrelation of photo counts over collection intervals separated by the autocorrelation interval t. In this case, t equals Δt, the collection interval (1 ms for the present example). Only fluctuations which are autocorrelated over at least one collection interval contributed to this measure of the degree of fluctuations.

The results are given in Table I. Each of five whole blood samples was assayed five times; the five samples consisted of a strong positive (A₁), a weak positive (A₂B), a very weak positive (weak A₂B) and two negatives (B and O). In each case, the mean and standard deviation of the five replicates are given for both methods of fluctuation analysis.

TABLE I

| | Method of invention (C.V.)p | | Known method (C.V.)T | |
|---|---|---|---|---|
| | mean | st'd. dev. | mean | st'd. dev. |
| Positives | | | | |

TABLE I-continued

|  | Method of invention (C.V.)$_p$ | | Known method (C.V.)$_T$ | |
| --- | --- | --- | --- | --- |
|  | mean | st'd. dev. | mean | st'd. dev. |
| A$_1$ | 16.8 | 1.7 | 23.2 | 1.2 |
| A$_2$B | 12.3 | 0.6 | 19.8 | 0.3 |
| weak A$_2$B | 8.1 | 0.5 | 17.2 | 0.3 |
| Negatives |  |  |  |  |
| B | 4.0 | 0.3 | 15.1 | 0.5 |
| O | 4.2 | 0.4 | 16.1 | 1.0 |

The method of the invention allowed the weakest postive to be well resolved. Clearly, all of the separation between the negatives and the weakest positive was lost when the known method was used.

Usually, a threshold between negative and positive results is established at the mean plus three standard deviations, using the distribution of all negative results. For the above example, the threshold was at 5.2 for the method of the invention and 18.4 for the known method. With the method of the invention, all five assays with the weak A$_2$B would have recorded positive, and the lowest single positive result (at 7.3) was separated from this threshold by fully six standard deviations, whereas, none of the individual five assays with the weak A$_2$B sample would have recorded as a positive using the known method.

It is evident from the above results that the subject method provides a simple accurate way for determining low concentrations of a wide variety of ligands. The subject method is readily adaptable to a wide variety of assays employing fluorescent labels. In addition, the subject method can be applied to novel protocols involving the counting of fluorescent bodies where the bodies can all have substantially the same fluorescence or can have widely varying fluorescence. The equipment is simple, can be readily automated, and can provide for direct reading of the amount of analyte in the sample based on the observed signal.

The present method is an improvement over the prior art procedures where an autocorrelation function is used to distinguish between free and bound fluorescence in a homogeneous immunoassay technique using long correlation times equal to the period of repetitive samplings or the autocorrelation to zero sampling time. With respect to the first case, periodic sampling is not required in the present invention in which the sample can be mechanically scanned in a simple fashion. Also, the total measurement time is much shorter. In the present invention, with a collection interval of 1 ms, 1000 contributions to the autocorrelation function can be accumulated in 1 sec., whereas, with periodic sampling with a period of 1 sec., 1000 contributions to the autocorrelation function takes 1000 sec. With respect to the second case, the present technique eliminates the contributions of background Poisson fluctuations which can be many times larger than the specific signal associated with particles exhibiting weak fluorescence such as weakly labeled cells.

The present technique permits better sensitivity than the known technique because better discrimination of signal over background is obtained in the present method. Particles having a fluorescence intensity only slightly greater than that of the bulk medium can be detected. Alternative methods that achieve the same sensitivity as that obtained in the present method require very powerful lasers and flow systems. Conventional non-flow fluorescence detection techniques cannot provide such a level of sensitivity without very long measurement times.

Although the foregoing invention has been described in some detail by way of illustration and example for purposes of clarity and understanding, it will be obvious that certain changes or modifications may be practiced within the scope of the appended claims.

What is claimed is:

1. In a method for measuring intensity fluctuations of an electromagnetic signal from a liquid medium, the improvement which comprises autocorrelating the intensity fluctuations of said signal over a single non-zero correlation interval of a duration which is short compared to the mean duration of said intensity fluctuations.

2. The method of claim 1 wherein said electromagnetic signal is produced by fluorescence emission.

3. The method of claim 1 wherein said intensity fluctuations are autocorrelated over an interval having a duration that is one-third to one-one hundredth the mean duration of said fluctuations.

4. In a method for measuring fluctuations of fluorescence intensity values in a liquid medium where such fluctuations are a result of the presence in said liquid medium of fluorescent particles, the improvement which comprises autocorrelating over a single correlation interval fluorescence intensity values obtained at a plurality of collection intervals wherein temporally adjacent collection intervals provide values for the fluoresence intensity of partially overlapping volumes of said liquid medium, wherein each of such volumes contains relatively few fluorescent particles, wherein the duration of any of said collection intervals is less than the mean residence time of a fluorescent particle within said volume and wherein the duration of the correlation interval is equal to, or is a finite but small multiple or a fraction of, the duration of any of said collection intervals and is short compared to the mean duration of the fluctuations.

5. The method of claim 4 wherein said fluorescence intensity of the values are obtained using an optical fiber probe.

6. The method of claim 4 wherein the duration of said single correlation interval is one-third to one-one hundredth the mean residence time of a fluorescent particle within said volume.

7. The method of claim 4 in which the amount of an analyte in a sample suspected of containing such analyte is determined and the fluctuations in fluorescence intensity values of said sample are compared to the fluctuations in fluorescence intensity values of a reference sample.

8. A method for determining an analyte in a sample suspected of containing said analyte, which method comprises—
 (a) combining said sample with an assay reagent to provide an assay mixture containing fluorescent particles where the fluorescent intensities of said particles are related to the presence of said analyte,
 (b) irradiating sequentially a plurality of partially overlapping volume of said sample with a wavelength of light between about 250 nm and 1200 nm, any of said irradiated sample volumes having relatively few fluorescent particles,
 (c) determining the fluorescence intensity values at a plurality of equal fluorescence collection intervals, the duration of any of said fluorescence collection intervals being less than the mean residence time of a fluorescent particle within said irradiated sample volume, (d) autocorrelating the fluorescence intensity values at said collection intervals over a single correlation time interval having a duration which is equal to, or is a small multiple for a fraction of, the duration of any of said collection intervals and which is short compared to the mean residence time of a fluorescent particle with said irradiated sample volume, and (e) relating the autocorrelated fluorescence intensity values to similarly autocorrelated fluorescence intensity values from an assay medium having a known amount of analyte.

9. The method of claim 8 wherein said irradiated sample volume is determined as a result of light from an optical fiber immersed in said assay mixture.

10. The method of claim 8 wherein the duration of said single correlation time interval is equal to or greater than the duration of one collection interval and less than the mean residence time of a fluorescent particle within said irradiated sample volume.

11. The method of claim 8 wherein the duration of said single correlation time interval is one-third to one-one hundredth the mean residence time of a fluorescent particle within said irradiated sample volume.

12. The method of claim 8 wherein the fluorescent particle is a red blood cell.

13. The method of claim 8 wherein the fluorescent particle is a latex bead.

14. The method of claim 8 wherein the fluorescence of said particle is modulated by means of ligand-receptor binding.

15. The method of claim 14 wherein the ligand-receptor binding is immunochemical.

16. The method of claim 8 wherein said irradiated sample volume has the characteristic of containing on the average one fluorescent particle.

17. The method of claim 8 wherein said autocorrelated fluorescence intensity values are a function of the degree of aggregation of particles.

18. The method of claim 17 wherein said particles are fluorescent.

19. The method of claim 8 wherein said autocorrelated fluorescence intensity values are a function of binding of a fluorescent particle to a non-fluorescent particle.

20. The method of claim 8 wherein a component of said sample is a biological fluid.

21. The method of claim 8 wherein the size of the fluorescent particles is between about 0.1 to 10 microns.

22. A method for determining an analyte in a sample suspected of containing said analyte, where said analyte is a member of a specific binding pair ("sbp member") consisting of ligand and its homologous receptor, which method comprises—

(a) combining said sample with an assay reagent to provide an assay mixture containing fluorescent particles which result from the binding between sbp members in proportion to the amount of analyte in said medium, (b) irradiating sequentially a plurality of partially overlapping volumes of said sample with a wavelength of light between about 250 nm and 1200 nm by means of an optical fiber, (c) determining the fluorescence intensity values at a plurality of equal fluorescence collection intervals, the duration of said fluorescence collection intervals being $\frac{1}{3}$ to 1/10 the mean duration of said fluctuations, (d) continuously autocorrelating at a single non-zero correlation interval the fluorescence intensity values at said collection intervals, and (e) relating the autocorrelated fluorescence intensity values to similarly autocorrelated fluorescence intensity values from an assay medium containing a known amount of analyte.

23. An apparatus for determining an analyte in a sample suspected of containing said analyte, where said analyte is a member of a specific binding pair ("sbp member") consisting of ligand and its homologous receptor, which apparatus comprises—

(a) means for irradiating sequentially a plurality of partially overlapping volumes of said sample with a wavelength of light between about 250 nm and 1200 nm, said sample having been combined with an assay reagent to provide an assay mixture containing fluorescent particles which result from the binding between sbp members in proportion to the amount of analyte in said medium, (b) means for determining the fluorescence intensity values at a plurality of equal fluorescence collection intervals, the duration of said fluorescence collection intervals being less than the mean residence time of a fluorescent particle within an irradiated sample volume, (c) means for continuously autocorrelating at a single non-zero correlation interval the fluorescence intensity values at said collection intervals, and (d) means for relating the autocorrelated fluorescence intensity values to similarly autocorrelated fluorescence intensity values from an assay medium containing a known amount of analyte.

24. The apparatus of claim 23 wherein said means in (c) is hardware dedicated to continuously autocorrelate the fluorescence intensity values at said collection intervals.

25. The apparatus of claim 23 wherein said means in (c) is software for continuously autocorrelating the fluorescence intensity values at said collection intervals.

* * * * *